(12) United States Patent
Milo (10) Patent No.: US 8,852,169 B2
(45) Date of Patent: Oct. 7, 2014

(54) SUCTION DEVICE FOR EVACUATING FUMES

(75) Inventor: Anton G. C. Milo, Akron, OH (US)

(73) Assignee: Milo Medical IP, LLC, Akron, OH (US)

(*) Notice: Subject to any disclaimer, the term of this patent is extended or adjusted under 35 U.S.C. 154(b) by 61 days.

(21) Appl. No.: 13/020,449

(22) Filed: Feb. 3, 2011

(65) Prior Publication Data

US 2012/0015317 A1 Jan. 19, 2012

Related U.S. Application Data

(60) Provisional application No. 61/364,499, filed on Jul. 15, 2010.

(51) Int. Cl.
*A61C 17/10* (2006.01)
*A61C 17/06* (2006.01)

(52) U.S. Cl.
CPC .................................. *A61C 17/043* (2013.01)
USPC ................................ 604/540; 433/93; 433/91

(58) Field of Classification Search
CPC .... A61C 17/04; A61C 17/043; A61C 17/046; A61M 1/0023; A61M 1/0039
USPC .......................... 433/29, 91–97; 604/540–542
See application file for complete search history.

(56) References Cited

U.S. PATENT DOCUMENTS

| 2,697,432 | A | | 12/1954 | Scinta | |
|---|---|---|---|---|---|
| 2,756,742 | A | | 7/1956 | Barton | |
| 3,154,069 | A | | 10/1964 | Ring | |
| 4,064,873 | A | | 12/1977 | Swenson | |
| 4,192,071 | A | | 3/1980 | Erickson | |
| 4,213,451 | A | * | 7/1980 | Swenson | 600/215 |
| 4,562,832 | A | | 1/1986 | Wilder et al. | |
| 5,078,602 | A | * | 1/1992 | Honoshofsky | 433/91 |
| 5,281,134 | A | * | 1/1994 | Schultz | 433/91 |
| 5,460,626 | A | | 10/1995 | Krespi | |
| 6,254,591 | B1 | * | 7/2001 | Roberson | 604/541 |
| 8,029,280 | B2 | * | 10/2011 | Black et al. | 433/93 |
| 2010/0121152 | A1 | * | 5/2010 | Boedeker | 600/187 |

OTHER PUBLICATIONS

International Search Report for International Application No. PCT/US2011/023619.

* cited by examiner

*Primary Examiner* — Philip R Wiest
*Assistant Examiner* — Benjamin Klein
(74) *Attorney, Agent, or Firm* — Calfee Halter and Griswold LLP (57) ABSTRACT

A suction device for evacuating fumes includes a tongue depressor having a pair of opposed walls; at least one suction tube connected to the tongue depressor; an elongated support member to which the suction tube is connected; and a connecting member attached to an end of the suction tube for connecting the suction tube to a suction generating device. A light such as a fiber optic light can be added to the suction device. The tongue depressor, suction tube and elongated support member can be made of one piece.

22 Claims, 8 Drawing Sheets

SUCTION DEVICE FOR EVACUATING FUMES

CLAIM OF PRIORITY

This application claims priority from Provisional Application Ser. No. 61/364,499 filed on Jul. 15, 2010, which is hereby entirely incorporated by reference.

BACKGROUND OF THE DISCLOSURE

The disclosure relates generally to the field of surgical instrumentation and more particularly, to a suction device to be used with a tongue blade device for evacuating cauterization tissue and fumes from a patient's mouth during oral laser surgery.

Electrocautery devices and surgical lasers are typically used for cutting or ablating tissues in various confined body cavities. For example, in the surgical treatment of snoring, the surgeon performs a vertical resection of the soft palate on both sides of the uvula, sparing the uvula itself, with further ablation with the laser of the lateral and inferior sides of the uvula to create a "new uvula" that is higher and smaller (uvulopalatoplasty). Electrocautery devices and surgical lasers are also used for reshaping or removing the tonsils (tonsillectomy), and for removing or reshaping posterior parts of the tongue (glossectomy).

During such applications of electrocautery devices and surgical lasers, it is desirable and necessary that the work area be maintained as free from smoke and vaporized tissue as possible. A tongue blade evacuation system can be provided as shown in U.S. Pat. No. 5,460,626, which is hereby incorporated by reference. It is also necessary that the patient's tongue be kept away from the working area. These requirements are necessary to provide a clear view of the working area for the surgeon.

While existing pharyngeal handpieces remove some of the smoke and vaporized tissue during laser application, they do not remove it rapidly enough to keep the area fully visible for the doctor or to prevent contamination of the lens. Additionally, while existing tongue depressors prevent the patient's tongue from interfering with the operation, they occupy one of the surgeon's hands while not effectively assisting with removal of fumes and tissue during surgery. Further, while the foregoing problems are particularly troublesome with respect to the above described applications for surgical lasers, they are also present to some degree in many other applications of surgical lasers.

In a preferred embodiment, the device is a tongue blade used with a McIvor mouthgag. The device is used intraoperatively to retract the tongue and mandible and open the mouth for surgeries involving the oral cavity/oropharynx. The device is preferably a one-piece surgical stainless steel unit with a built-in suction tube to evacuate any anesthetic gases or noxious/dangerous fumes or plumes generated by electrocautery, or other similar devices. This serves as a protective feature to help ensure the safety of the Operating Room Staff and the patient. It can also be used to oxygenate or jet ventilate a patient intraoperatively by passing oxygen through the suction passage down into the oral cavity/oropharynx. There can be two other variations of the device: a high impact plastic model that is disposable, and a stainless steel model with a removable, disposable suction tubing.

It is accordingly an object of the present disclosure to provide a tongue blade suction device for eliminating or reducing the foregoing problems during surgical applications while providing better overall results.

SUMMARY OF THE DISCLOSURE

The disclosure relates to an apparatus for removing noxious fumes. In particular, it relates to an apparatus for and a method of removing noxious fumes, plumes generated by electrocautery, smoke and vaporized tissue from a patient's mouth and controlling a patient's tongue through the use of a one-piece tongue blade coupled with a suction device to form a single unit which can be used in and during surgical applications. Specifically, the disclosure includes an adjustable tongue blade coupled with a suction device.

In accordance with one aspect of the disclosure, a suction device for evacuating fumes has a tongue depressor including a pair of opposed walls; a suction tube connected to the tongue depressor; an elongated support member to which the suction tube is connected; and a connecting member attached to an end of the suction tube for connecting the suction tube to a suction generating device.

It is another object of the disclosure to provide a more efficient system for controlling a patient's tongue and for removing noxious fumes, smoke and vaporized tissue or plumes generated by electrocautery from a patient's mouth during surgery.

It is another object of the disclosure to provide a device combining a tongue blade and suction device as a single tool to increase the rate of noxious fumes, smoke and vaporized tissue evacuation from a patient's mouth during surgery.

It is still another object of the disclosure to provide a method of controlling a patient's tongue and evacuating noxious fumes, plumes generated by electrocautery, smoke and vaporized tissue from a patient's mouth during surgery.

It is another object of the device to provide a removable and disposable suction tube.

It is still another object of the disclosure to provide a one-piece tongue blade and suction device made of disposable plastic.

It is another object of the disclosure to provide a suction tube and fiber optic light and two receiving rings on the tongue blade for retaining the tube and light.

Still other objects of the disclosure will become apparent upon a reading and understanding of the following detailed description.

BRIEF DESCRIPTION OF THE DRAWINGS

For a fuller understanding of the nature and objects of the disclosure, reference should be made to the following detailed description and accompanying drawings, in which.

DETAILED DESCRIPTION OF THE DISCLOSURE

Figures 1, 1A:
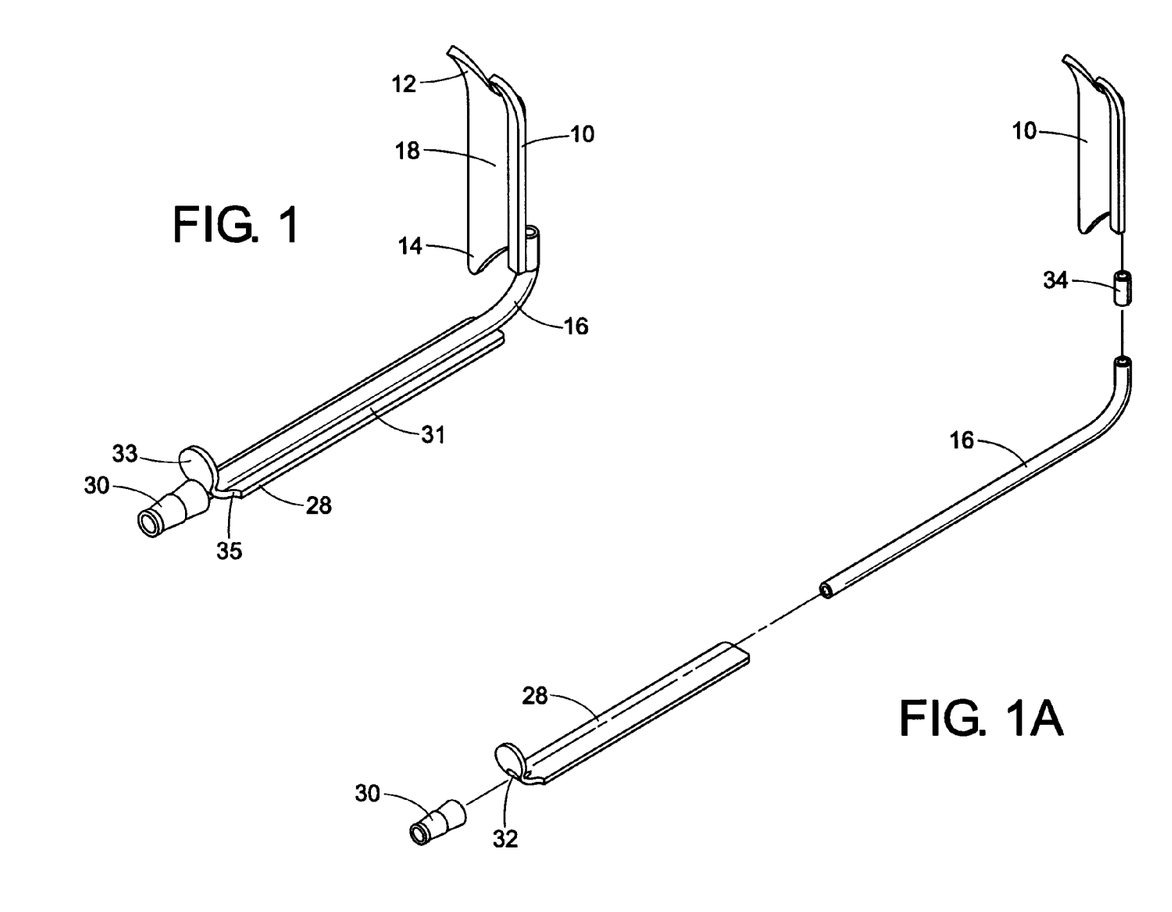
FIG. 1 is a perspective view of a tongue blade with a suction device in accordance with a preferred embodiment of the invention.
FIG. 1A illustrates an exploded view of a tongue blade with a suction device in accordance with the disclosure.
Figure 1B:
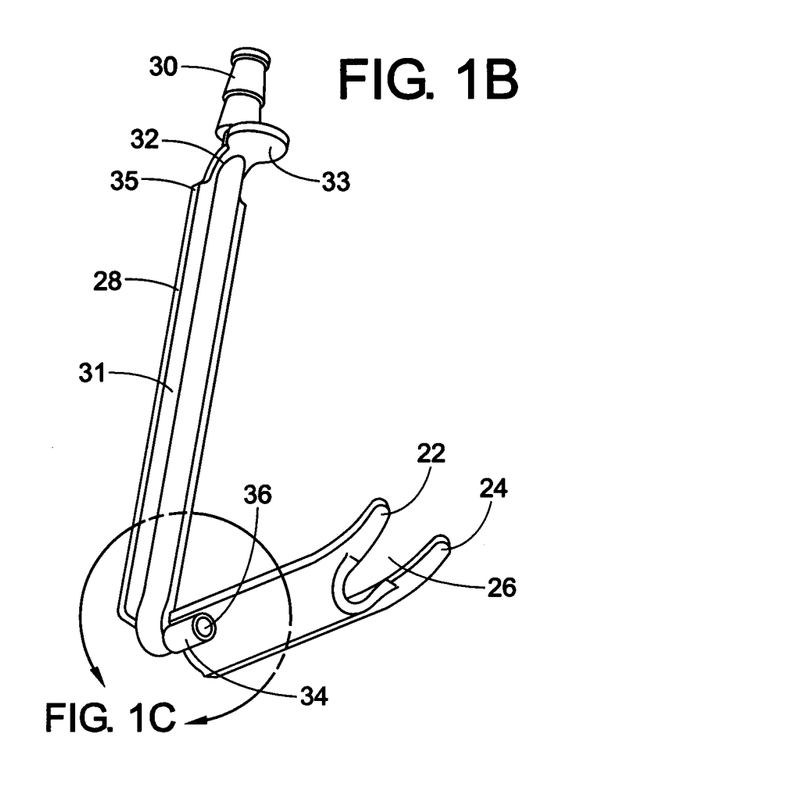
FIG. 1B is another perspective view of the tongue blade and suction device of FIG. 1.
Figure 1C:
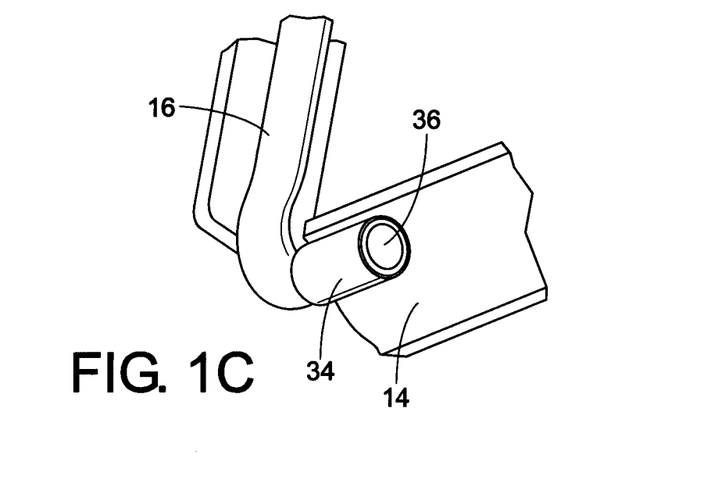
FIG. 1C is a detail view of FIG. 1B.

FIGS. 1-1C show illustrations of a preferred embodiment of the disclosure including a tongue blade 10 having a distal end 12 for inserting into a patient's mouth during a surgical application and a proximal end 14 coupled in communication with a hollow tube 16. The tongue blade has a curved or rounded or offset shape body 18 (or other shapes) which acts as a tongue depressor and rests on the patient's tongue. The distal end 12 has a fork or U-shaped appearance formed by two protrusions 22, 24 (FIG. 1B) extending therefrom which form a channel or opening 26. protrusions 22, 24 extend or curve upwardly as seen in FIG. 1B.

A disposable hollow suction tube 16 such as plastic or rubber or other flexible material is connected to an elongated spine 28 which is in communication with a barb or hollow connector 30. The spine is preferably formed from stainless steel or any other suitable rigid material. The spine has a first elongated portion 31 and a shorter portion 33 which extends at about 90 degrees or so from end 35 of portion 31. Portion 33 has an opening 32 for receiving the tube 16 therethrough. Further, in the embodiment illustrated in FIG. 1C, the suction tube 16 has a receiving outlet member 34 having an opening 36 formed therethrough located adjacent to the proximal end 14 of the blade for removing anesthetic gases, noxious fumes, smoke, vaporized tissue, plumes generated by electrocautery and other debris from a patient's mouth during use in surgery.

When in use, smoke, plumes generated by electrocautery, noxious fumes and vaporized tissue removal is effectuated by attaching barb or connector 30 to any pneumatic device (not shown) typical of the art which causes a suction effect from the tongue blade.

While the surgical application is taking place, the spine 28 is held in the patient's mouth directing the suction tube 16 into the patient's mouth which removes smoke, fumes, plumes generated by electrocautery, and vaporized tissue from the patient's mouth using opening 36 (FIG. 1 B). Meanwhile, the tongue blade 10, which is connected to the tube, is in the patient's mouth controlling the patient's tongue, thus preventing the tongue from obstructing the application of the suction tube and removing smoke and vaporized tissue at the same time. The tongue blade suction tube 16 evacuates the smoke, fumes, plumes generated by electrocautery, and vaporized tissue by sucking it through the receiving port or opening 36, through tube 16, and out through any well known pneumatic or other suction causing device (not shown), attached to the tube barb 30.

In a preferred embodiment, the device is a tongue blade 10 used with a McIvor mouthgag. The device is used intraoperatively to retract the tongue and mandible and open the mouth for surgeries involving the oral cavity/oropharynx. The device 10 is preferably a one-piece surgical stainless steel tongue blade with a built-in suction tube 16 to evacuate any noxious/dangerous fumes or plumes generated by electrocautery, or other similar devices. This serves as a protective feature to help ensure the safety of the Operating Room Staff as well as the patient.

Alternatively, the tongue blade and suction device can also be used to oxygenate or jet ventilate a patient intraoperatively by passing oxygen through the suction tube 16 down into the oral cavity/oropharynx through opening 36.

Figure 2:
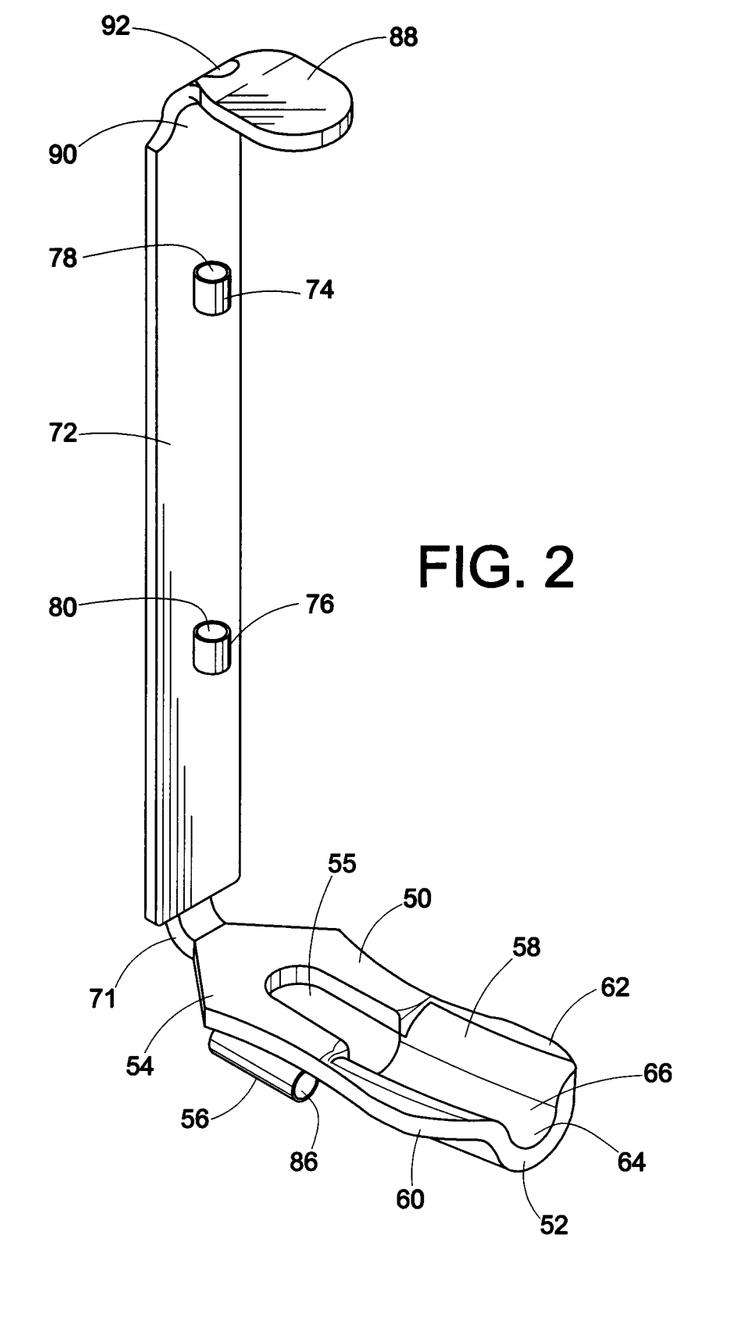
FIG. 2 is a perspective view of a tongue blade with a suction device in accordance with another embodiment of the disclosure.
Figure 2A:
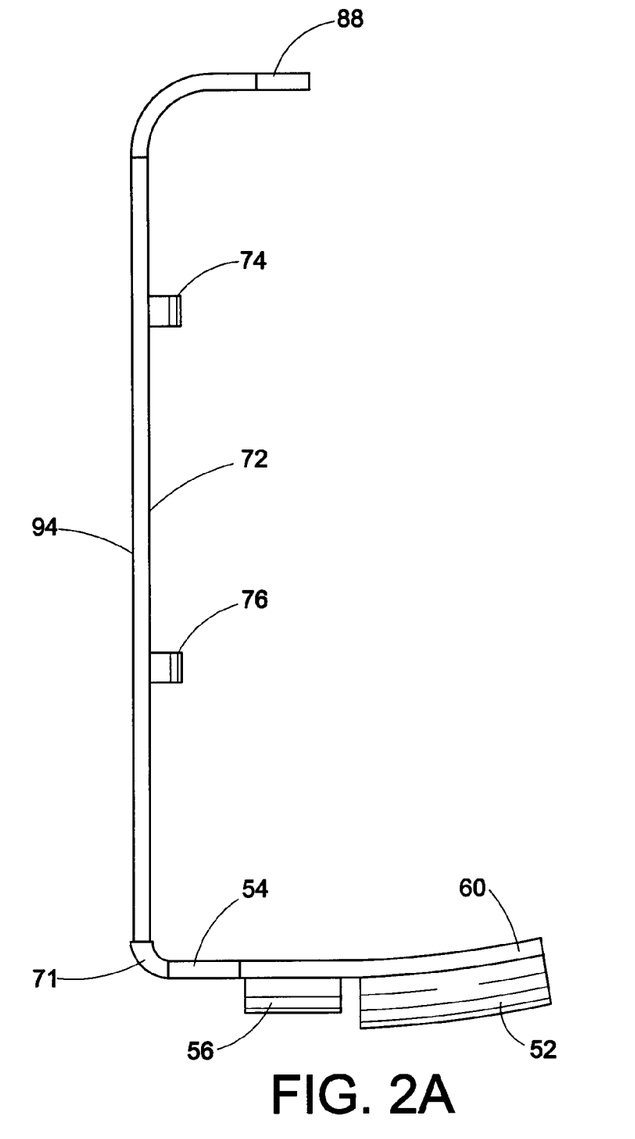
FIG. 2A is a side elevational view of the tongue blade of FIG. 2.
Figure 2B:
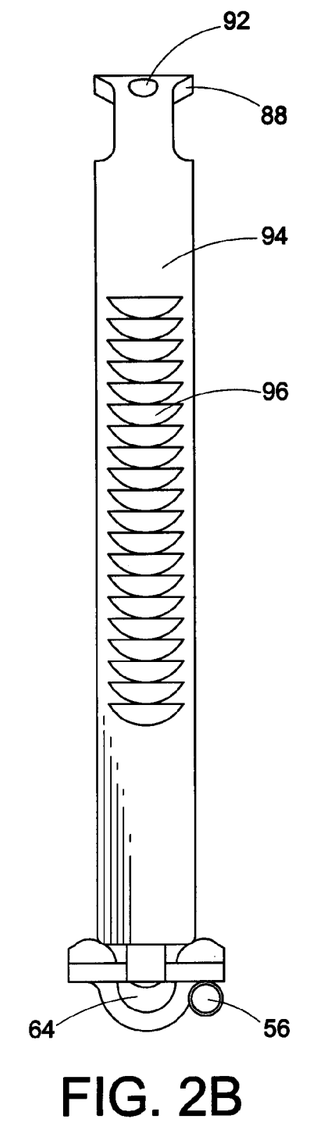
FIG. 2B is a rear elevational view of the tongue blade of FIG. 2.
Figure 3:
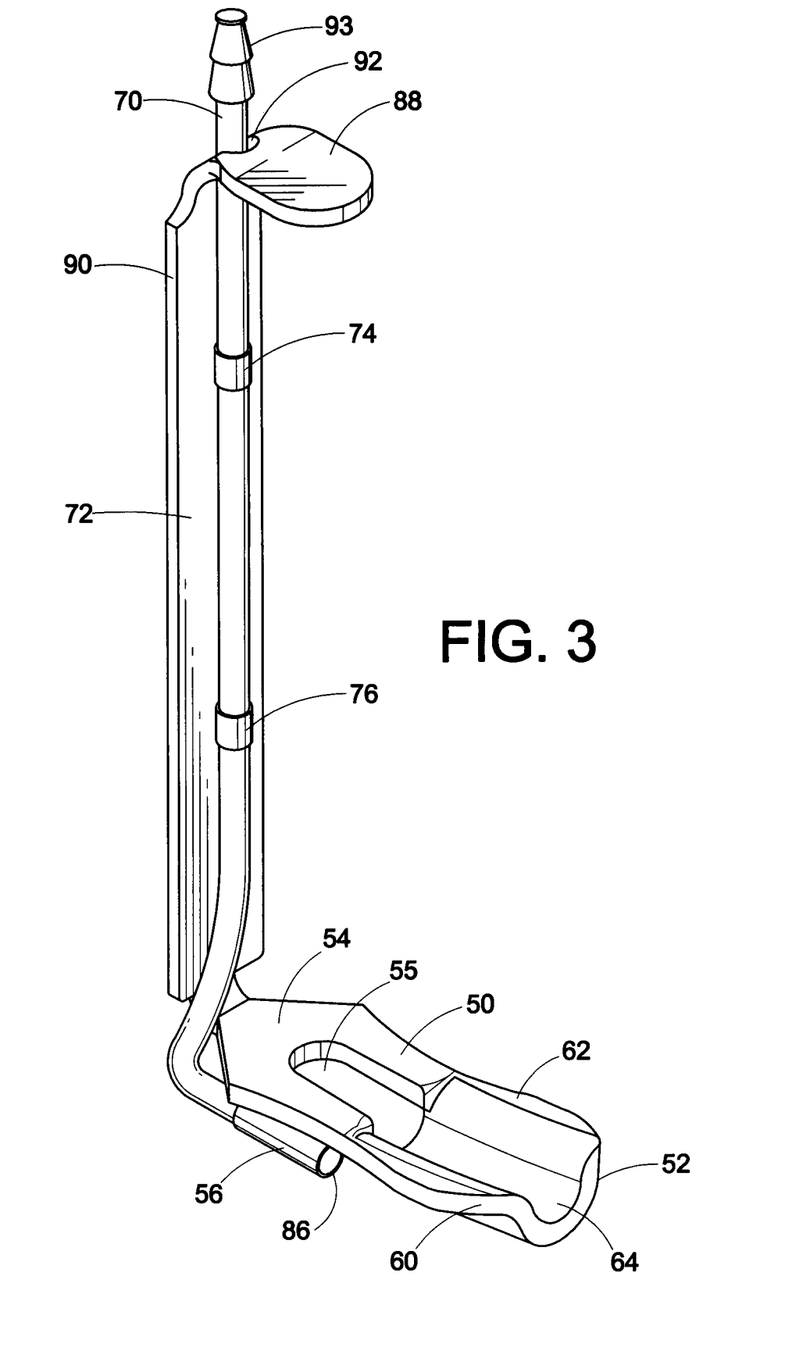
FIG. 3 is a perspective view of the tongue blade and suction device of FIG. 2 with a suction tube attached.
Figure 5:
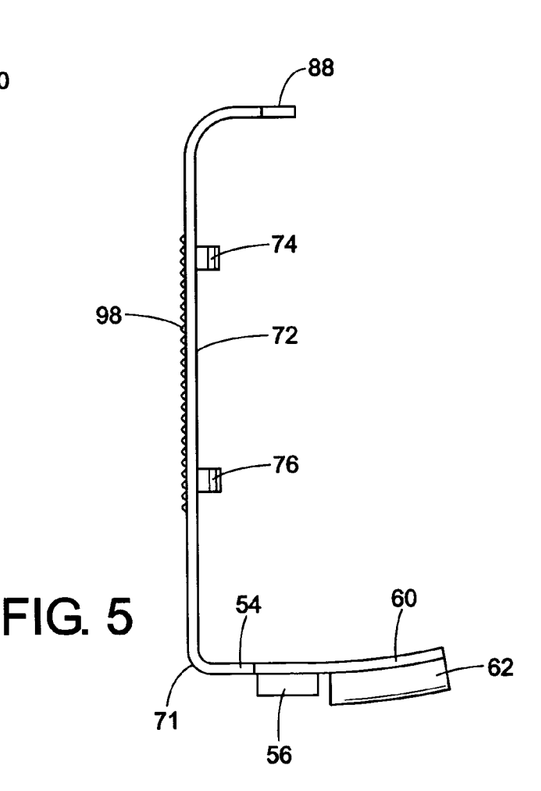
FIG. 5 is a side elevational view of a tongue blade and suction device with gripping members formed thereon.

FIGS. 2-2B and 3 show illustrations of an alternate embodiment of the disclosure including a tongue blade 50 having a distal end 52 for inserting into a patient's mouth during a surgical application and a proximal end 54 coupled with a hollow tube receiving member 56 and an elongated support member or back wall or spine 70 via a curved connector 71. A substantially U-shaped opening 55 is formed near end 54. The tongue blade has a curved or rounded shape body 58 which acts as a tongue depressor and rests on the patient's tongue. The distal end 52 has a fork or U-shaped appearance formed by two protrusions or walls 60, 62 extending therefrom which form a rounded or curved channel 64 having opening 66. Walls 60, 62 curve upwardly as seen in FIG. 2A. A hollow disposable suction tube 70 is connected to elongated spine or back wall 72 and is in fluid communication with hollow connector or receiving member 56. The spine has a pair of cylindrical shaped members 74, 76 having openings 78, 80 formed therein for receiving the tube 70 therein. Further, in the embodiment illustrated in FIG. 2, the suction tube receiving outlet member 56 has an opening 86 located adjacent to the proximal end 54 of the blade for removing noxious fumes, smoke, vaporized tissue, plumes generated by electrocautery and other debris from a patient's mouth during use in surgery. Spine 72 also has a wall 88 extending from end 90 which has an opening 92 therethrough for receiving tube 70. Wall 88 is bent at approximately 90 degrees or so with respect to spine 72. On a rear side 94 of the spine are formed a plurality of gripping notches or knurl recesses 96 which provide points of attachment or a grip to hold the spine during use with a mouth gag. Alternatively, referring to FIG. 5, gripping members, protrusions or extensions 98 can be provided to also provide a grip to form a self-retaining unit in the patient's mouth or throat.

When in use, smoke, plumes generated by electrocautery, noxious fumes and vaporized tissue removal is effectuated by attaching barb or connector 93 (FIG. 3) to a pneumatic device typical of the art which causes a suction effect from the tongue blade.

While the surgical application is taking place, the spine 72 is held in the patient's mouth directing the suction tube 70 in the patient's mouth and removing smoke, fumes, plumes generated by electrocautery, and vaporized tissue via opening 86. The tongue blade 50, which is connected to the tube, is in the patient's mouth controlling the patient's tongue, thus preventing it from obstructing the application and removing smoke and vaporized tissue at the same time. The tongue blade suction tube 70 meanwhile evacuates the smoke, fumes, plumes generated by electrocautery, and vaporized tissue by sucking it through the receiving port or opening 86, through tube 70, and out through the pneumatic or other suction causing device (not shown) attached to barb 93. After use, the suction tube 70 can be removed and discarded. The spine 72 can be sanitized and reused with a new suction tube.

Another variation of the disclosure is a one-piece unit which is fabricated from a high impact plastic that is disposable.

Figure 4:
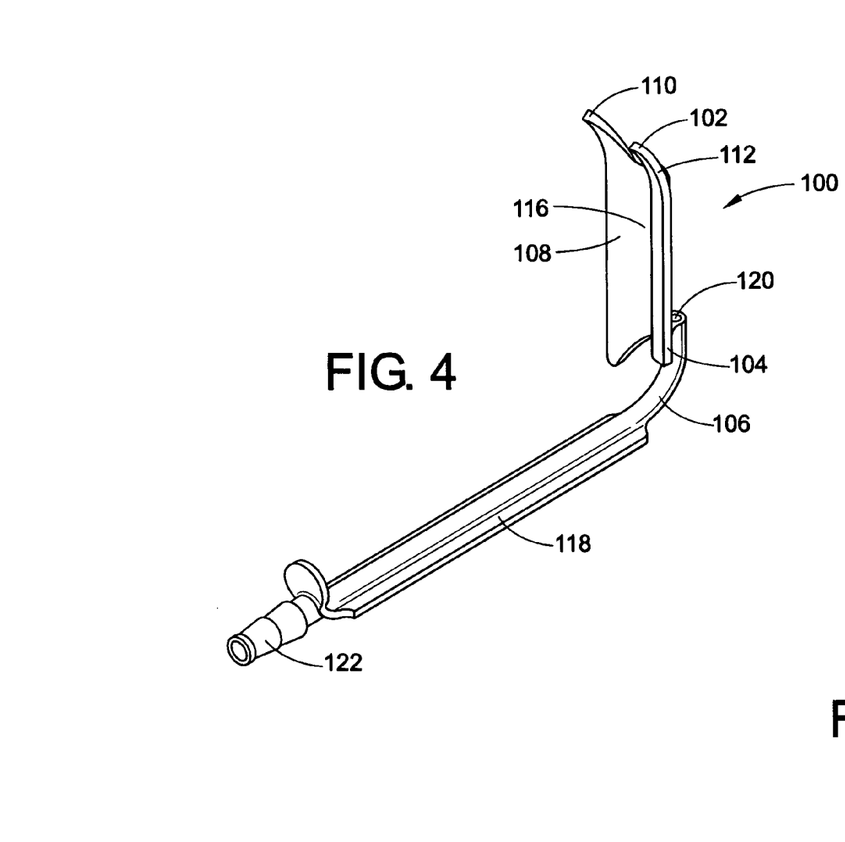
FIG. 4 is a perspective view of a one-piece tongue blade and suction device in accordance with another aspect of the disclosure.

FIG. 4 shows an illustration of an alternate embodiment of the disclosure for a one-piece tongue blade and suction device which can be disposable and fabricated of thermoplastic or any other suitable material. The device includes a tongue blade 100 having a distal end 102 for inserting into a patient's mouth during a surgical application and a proximal end 104 coupled in fluid communication with a hollow tube 106 integrally formed with the tongue blade. The tongue blade has a curved or rounded shape body 108 which acts as a tongue depressor and rests on the patient's tongue. The distal end 102 has a fork or U-shaped appearance formed by two protrusions 110, 112 extending therefrom and curved upwardly which form a channel or opening 116 therebetween. The hollow tube 106 extends from an elongated spine 118. The suction tube 106 has an opening 120 located adjacent to the proximal end 104 of the blade for removing noxious fumes, smoke, vaporized tissue, plumes generated by electrocautery and other debris from a patient's mouth during use in surgery.

When in use, smoke, plumes generated by electrocautery, noxious fumes and vaporized tissue removal is effectuated by attaching connector end 122 of tube 106 to a pneumatic device typical of the art which causes a suction effect from the tongue blade.

While the surgical application is taking place, the spine 118 is held in the patient's mouth directing the suction tube 106 in the patient's mouth and removing smoke, fumes, plumes generated by electrocautery, and vaporized tissue via opening 120. Meanwhile, the tongue blade 100, which is connected to the tube, is in the patient's mouth controlling the patient's tongue, thus preventing it from obstructing the application and removing smoke and vaporized tissue at the same time. The tongue blade suction tube 106 meanwhile evacuates the smoke, fumes, plumes generated by electrocautery, and vaporized tissue by sucking it through the receiving port or opening 120, through tube 106, and out through any well known device the pneumatic or other suction causing device (not shown), attached to the tube barb 122.

Figure 6A:
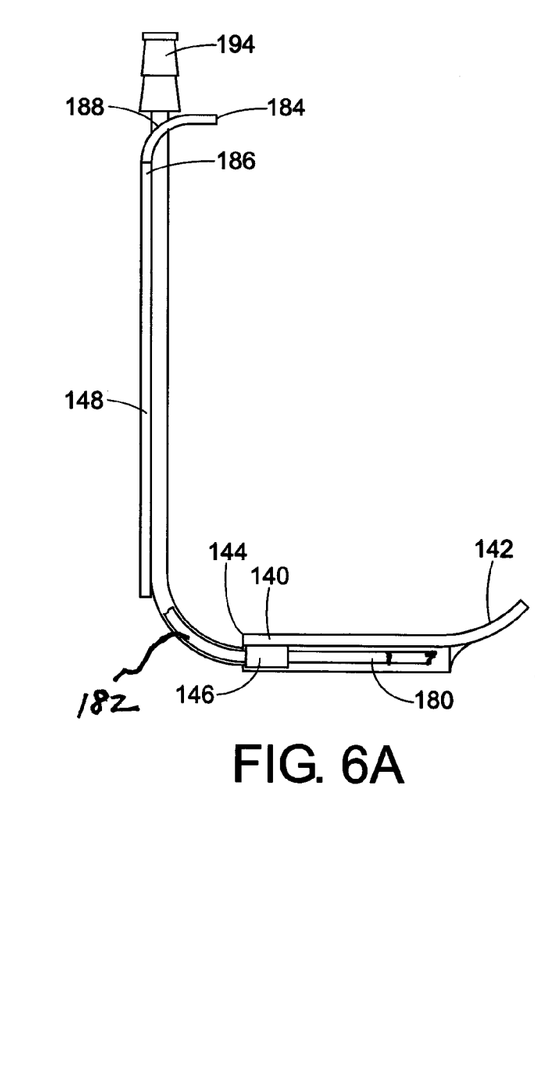
FIG. 6A is a side elevational view of another embodiment of the disclosure with a suction tube and a fiber optic light.
Figure 6B:
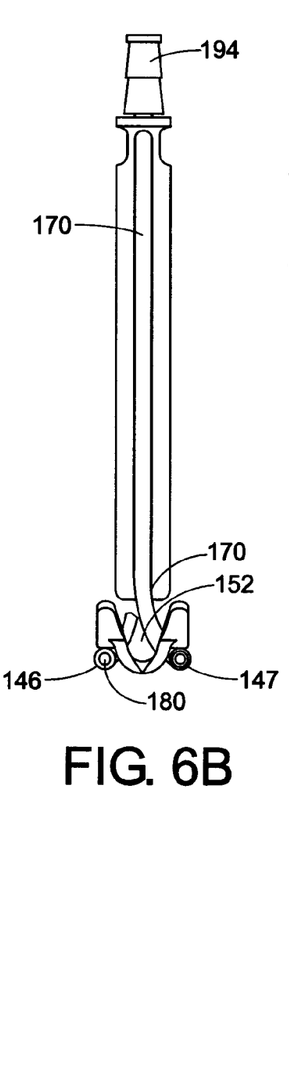
FIG. 6B is a front elevational view of the device of FIG. 6A.
Figure 6C:
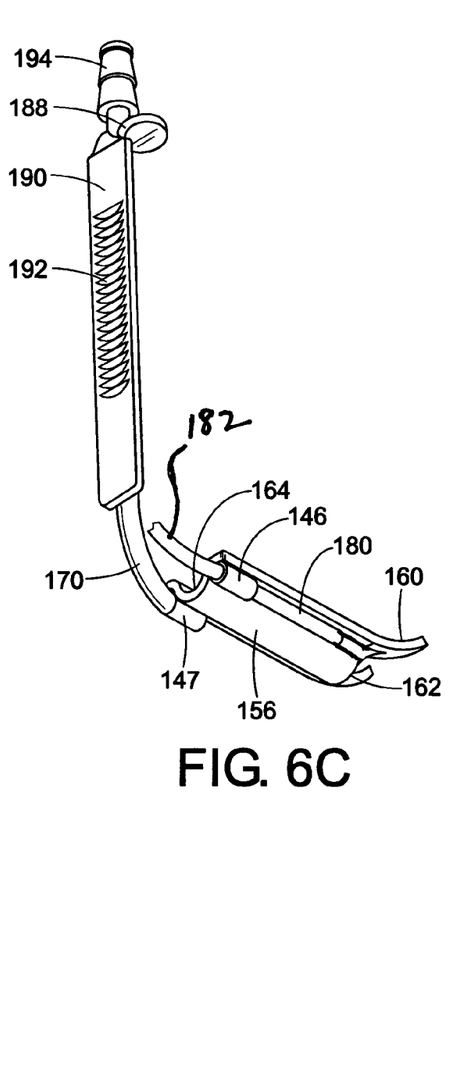
FIG. 6C is a rear perspective view of the device of FIG. 6A.

Referring now to FIGS. 6A-6C, another alternate embodiment of the suction device is shown. The device is preferably used with a Dingman mouthgag such as used in plastic surgery. A fiber optic light also can be added to the device. This device can be one-piece and disposable as well.

FIGS. 6A-6C show illustrations of an alternate embodiment of the disclosure including a tongue blade 140 having a distal end 142 for inserting into a patient's mouth during a surgical application and a proximal end 144 coupled with a hollow tube receiving members 146 and a ring or receiving member 147 for connecting a light such as a fiber optic light 180 and an elongated support member or spine 148. A substantially U-shaped opening 152 is formed in blade 140. The tongue blade has a curved or rounded shape body 156 which acts as a tongue depressor and rests on the patient's tongue. The U-shaped appearance is formed by two protrusions or walls 160, 162 extending therefrom which form a rounded or curved channel 164. Walls 160, 162 curve upwardly as seen in FIG. 6A. Hollow disposable suction tube 170 is connected to elongated spine 148 and is in fluid communication with hollow connector or receiving member 147. Further, in the embodiment illustrated in FIG. 6C, the ring or receiving outlet member 146 accommodates a light such as a fiber optic light 180 extending therefrom. Fiber optic light 180 can be attached via ring 146 for illuminating the patient's mouth. A connecting wire 182 extends from the light to an external power source (not shown).

Tube 170 is located adjacent to the proximal end 142 of the blade for removing anesthetic gases, noxious fumes, smoke, vaporized tissue, plumes generated by electrocautery and other debris from a patient's mouth during use in surgery. Spine 148 also has a wall 184 extending from end 186 which has an opening 188 therethrough for receiving tube 170. Wall 184 is bent at approximately 90 degrees with respect to spine 148. On a rear side 190 of the spine are formed a plurality of gripping notches or knurl recesses 192 which provide a grip to hold the spine. Alternatively, gripping members, protrusions or extensions can also be provided to also provide an ergonomic grip.

When in use, smoke, plumes generated by electrocautery, noxious fumes and vaporized tissue removal is effectuated by attaching barb or connector 194 to a pneumatic device typical of the art which causes a suction effect from the tongue blade.

Figure 7A:
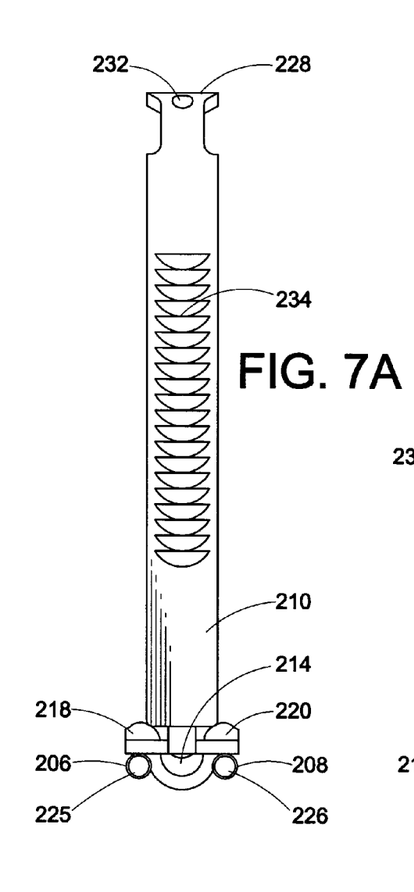
FIG. 7A is a rear elevational view of another embodiment of the disclosure with a suction tube receiving member and a fiber optic light receiving member.
Figure 7B:
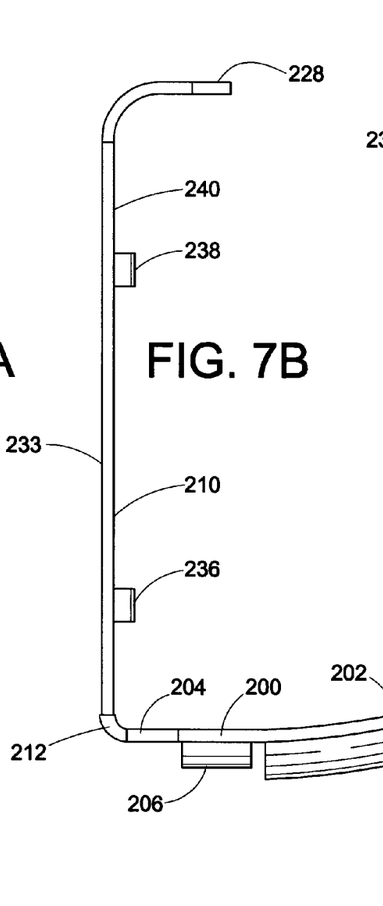
FIG. 7B is a side elevational view of the device of FIG. 7A.
Figure 7C:
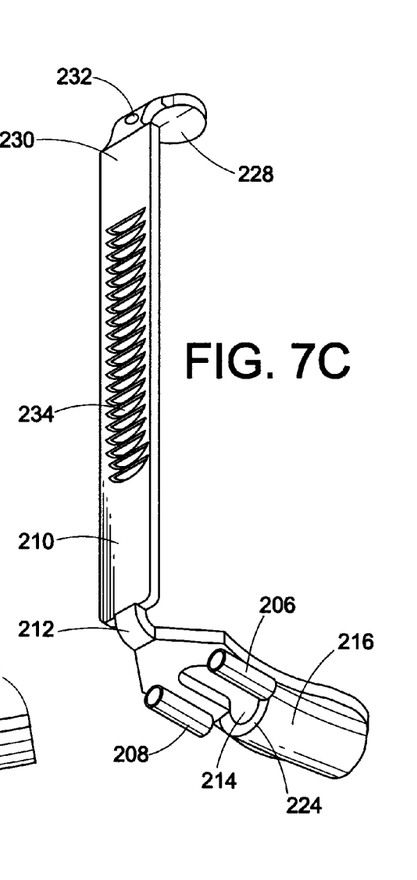
FIG. 7C is a rear perspective view of the device of FIG. 7A.

Referring now to FIGS. 7A-7C, another alternate embodiment of the suction device is shown.

FIGS. 7A-7C show illustrations of an alternate embodiment of the disclosure including a tongue blade 200 having a distal end 202 for inserting into a patient's mouth during a surgical application and a proximal end 204 coupled with a pair of hollow tube receiving members 206, 208 and an elongated support member or spine 210 via a curved connector 212. A substantially U-shaped opening 214 is formed in blade 200. The tongue blade has a curved or rounded shape body 216 which acts as a tongue depressor and rests on the patient's tongue. The distal end 202 has a fork or U-shaped appearance formed by two protrusions or walls 218, 220 extending therefrom which form a rounded or curved channel 224 having opening 214. Walls 218, 220 curve upwardly as seen in FIG. 7B. A hollow disposable suction tube is connected to elongated spine 240 and is in fluid communication with one of hollow connector or receiving members 206, 208, such as shown in FIGS. 6A-6C. Further, in the embodiment illustrated in FIGS. 7A-7C, the suction tube receiving outlet members 206, 208 have openings 225, 226 located adjacent to the proximal end 204 of the blade for removing anesthetic gases, noxious fumes, smoke, vaporized tissue, plumes generated by electrocautery and other debris from a patient's mouth during use in surgery when a suction tube is installed. One of the members 206, 208 can also accommodate a light such as a fiber optic light as shown in the embodiment of FIGS. 6A-6C. The spine also has a wall 228 extending from end 230 which has an opening 232 therethrough for receiving portions of suction tubes or fiber optic lights therein. Wall 228 is bent at approximately 90 degrees with respect to the spine. On a rear side 233 of the spine are formed a plurality of gripping notches or knurl recesses 234 which provide a grip to hold the spine in a self-retaining manner for use with a mouthgag. Alternatively, gripping members, protrusions or extensions can be provided to also provide a grip. Rings or receiving members 236 and 238 are formed on a first side 240 of wall 210 to accommodate or retain a suction tube or a fiber optic light.

When in use, smoke, plumes generated by electrocautery, noxious fumes and vaporized tissue removal is effectuated by attaching barb or connector 93 (FIG. 3) to a pneumatic device typical of the art which causes a suction effect from the tongue blade.

The exemplary embodiment has been described with reference to the preferred embodiments. Obviously, modifications and alterations will occur to others upon reading and understanding the preceding detailed description. It is intended that the exemplary embodiment and the appended claims be construed as including all such modifications and alterations.

The invention claimed is:

1. A suction device comprising:
a rigid hollow tube;
the rigid hollow tube having a first end for connecting to a suction source;
a spine extending along a first portion of the rigid hollow tube;
a second portion of the rigid hollow tube that is curved; and
a third portion of the rigid hollow tube having an inlet and a tongue blade secured thereto;
wherein the tongue blade has a first surface a second surface opposite the first surface;
wherein the first surface is located closer to the first end of the hollow tube for connecting to a suction source than the second surface;
wherein at least a part of the inlet of the rigid hollow tube is located above at least a portion of the second surface of the tongue blade;
wherein the second portion of the rigid hollow tube joins the spine and the tongue blade together and forces between the spine and the tongue blade are transferred through the second portion of the rigid hollow tube.

2. The suction device of claim 1, wherein the hollow tube is made of surgical stainless steel.

3. The suction device of claim 1, wherein the hollow tube is made of thermoplastic.

4. The device of claim 1, wherein said tongue blade comprises a body having an offset connection to the tube.

5. The device of claim 1, wherein said tongue blade comprises a pair of opposed walls that form a channel.

6. The device of claim 5, wherein the center line between said opposed walls are offset from the tube.

7. The suction device of claim 1, wherein said tongue blade comprises a retaining member for retaining a light.

8. The suction device of claim 7, wherein said retaining member comprises a ring.

9. The suction device of claim 7, wherein said retaining member comprises a cylindrical connecting member.

10. The suction device of claim 1, wherein said spine comprises a back wall.

11. The suction device of claim 1, wherein said hollow tube has only a single inlet member.

12. A suction device comprising:
a connection member for connecting to a suction source;
a hollow spine extending from the connection member;
the hollow spine extending along a longitudinal axis;
a curved tube extending from the hollow spine;
a tongue blade extending from the curved tube;
an opening at the end of the curved tube for air to flow through the curved tube, the hollow spine and the connection member;
the tongue blade having width and a thickness,
wherein the thickness extends along the longitudinal axis and the width is transverse to the longitudinal axis; and wherein the width is greater than the thickness;
wherein the opening at the end of the curved tube is located above the tongue blade;
wherein the curved tube is rigid and provides support for transfer of loads between the hollow spine and the connection member.

13. The suction device of claim 12, wherein said hollow tube has only a single inlet member.

14. The suction device of claim 12, wherein the curved tube is made of surgical stainless steel.

15. The suction device of claim 12, wherein the curved tube is made of thermoplastic.

16. The device of claim 12 wherein said tongue blade comprises a pair of opposed walls that form a channel.

17. The device of claim 16, wherein a centerline of said opposed walls is offset from the tube.

18. A suction device comprising:
a spine that extends substantially in a vertical direction;
the spine having a plurality of grip members extending substantially perpendicular to the spine;
a tongue blade;
the tongue blade having a first surface and a second surface opposite the first surface, wherein the first surface and the second surface extend in a horizontal direction and the distance between the first surface and the second surface is less than the distance across the first surface and
a hollow tube;
a portion of the hollow tube is curved and connects the spine and the tongue blade together;
the hollow tube having an opening, wherein at least a portion of opening of the hollow tube is located above the tongue blade;
the hollow tube providing structural support between the spine and the tongue blade;
a connection member for connecting a first end of the hollow tube to a suction source; and
wherein the first surface is located closer to the connection member than the second surface.

19. The suction device of claim 18, wherein the hollow tube is made of surgical stainless steel.

20. The suction device of claim 18, wherein the hollow tube is made of thermoplastic.

21. The suction device of claim 18, wherein said tongue blade comprises a body with an offset connection to the tube.

22. The suction device of claim 18, wherein said tongue blade comprises a pair of walls that form a channel.

* * * * *